United States Patent [19]

Lambers et al.

[11] Patent Number: 5,792,794
[45] Date of Patent: Aug. 11, 1998

[54] RETINOYLAMIDE BASED DERIVATIVES OF SPHINGOID BASES

[75] Inventors: Johannes W. J. Lambers, Pijnacker; Jan Verweij, Leiden, both of Netherlands

[73] Assignee: Gist-Brocades, N.V., Ma Delft, Netherlands

[21] Appl. No.: 809,460

[22] PCT Filed: Sep. 2, 1996

[86] PCT No.: PCT/EP96/03848

§ 371 Date: Apr. 21, 1997

§ 102(e) Date: Apr. 21, 1997

[87] PCT Pub. No.: WO97/09307

PCT Pub. Date: Mar. 13, 1997

[30] Foreign Application Priority Data

Sep. 1, 1995 [EP] European Pat. Off. ............ 95202369

[51] Int. Cl.$^6$ .................... A61K 31/20; C07C 233/09
[52] U.S. Cl. .................... 514/559; 514/844; 554/35; 554/61
[58] Field of Search .................... 554/61, 35; 514/559, 514/844

[56] References Cited

U.S. PATENT DOCUMENTS 5,190,876  3/1993  Merrill, Jr. et al. ............... 435/240.2
5,369,030  11/1994 Hannun et al. .................. 435/240.2
5,643,899  7/1997  Elias et al. ....................... 514/171

FOREIGN PATENT DOCUMENTS 0 009 776  7/1982  European Pat. Off.
2 081 447  12/1991 France.

OTHER PUBLICATIONS

Vitamins and the Skin, Bernard Idson,*Cosmetics and Toiletries*, vol. 108, pp. 79–88, Dec. 1993.
Sustained Improvement with Prolonged Topical Tretinoin (Retinoic Acid) for Photoaged Skin, by Charles N. Ellis, et al, Jour. of the Amer. Acad of Dermatology, vol. 23, No. 4, pp. 629–637, Oct. 1990.
Topical Tretinoin for Photoaged Skin, by Albert M. Kligman et al, Jour. of the Amer. Acad. of Dermatology, vol. 15, No. 4, Part 2, pp. 836–859, Oct. 1986.
Selected Therapeutic Applications of Topical Tretinoin, by Andree A. Haas, et al, Jour. of the Amer. Acad. of Dermatology, vol. 15, No. 4, Part 2, pp. 870–877, Oct. 1986.
Robson et. al., J. Lipid Research, vol. 35, pp. 2060–2068, 1994.

*Primary Examiner*—Shailendra Kumar
*Attorney, Agent, or Firm*—Morrison & Foerster

[57] ABSTRACT

The present invention relates to active derivatives of sphingoid bases. Specifically, the invention relates to retinoylamide based derivatives of sphingoid bases. The present invention describes a method for obtaining these compounds. The invention also relates to the use of these compounds in cosmetic compositions.

8 Claims, No Drawings

1

RETINOYLAMIDE BASED DERIVATIVES OF SPHINGOID BASES

This application is a 371 PCT/BA96/03848, filled Sep. 2, 1996.

FIELD OF THE INVENTION

The present invention relates to new compounds namely active derivatives of sphingoid bases. Specifically, the invention relates to retinoylamide based derivatives of sphingoid bases. The present invention describes a method for obtaining these compounds. The invention also relates to the use of these compounds in compositions for topical use.

BACKGROUND OF THE INVENTION

Vitamin A and its derivatives ("retinoids") have been widely used in cosmeticology and dermatology over the past two decades. According to the USP official monograph, the retinoids comprise retinol (vitamin A alcohol) or its esters, the corresponding aldehyde retinal, as well as the free acid retinoic acid, also called vitamin A acid or tretinoin. The role of retinoids in regulation of skin development seems best satisfied by retinoic acid. Thus, activity of retinol, retinal and other vitamin A derivatives such as retinyl-palmitate or -acetate may depend on their conversion to retinoic acid. This conversion depends on the enzymatic activity (e.g. ester cleavage and oxidation) present in the skin and it has been demonstrated that skin preparations can indeed convert retinol to retinoic acid (B. Idson, Cosm. & Toil. (1993), 108, pp.79–88).

Numerous studies have shown a broad range of physiological responses upon retinoid treatment. In general terms, a retinoid applied topically can be regarded as an agent which stimulates the skin both mitotically and metabolically. These effects include among others (Kretz, A., SÖFW (1993), 119, 21–24):

stimulation of the renewal process of epidermal cells which results in a thickening of the epidermis.

increase in the deposition of subepidermal collagen.

improvement of skin elasticity.

regulation of the keratinisation process.

angiogenesis.

Specifically, retinoic acid containing topical preparations have been developed for the treatment of:

acne (deblocking of the sebaceous glands) and psoriasis (normalising keratinisation) [Haas, A. A. and Arndt, K. A., (1986), J. Am. Acad. Dermatol., 15, pp. 870–877].

UV-damaged skin, reversing the cardinal signs of photodamage, such as wrinkles, brown (liver)spots, and skin surface roughness [Kligman, A.M. et al., (1986), J. Am. Acad. Dermatol., 15, pp. 836–859].

However, the use of retinoids as such, especially retinoic acid, has several drawbacks [Ellis, C. N., in Intensive Course in Dermato-cosmetic Sciences (1992), volume II, pp. 133–147]; [Ellis, C. N., J. Am. Acad. Dermatol. (1990), 23, pp. 629–637]

Retinoids are very unstable and sensitive to, amongst others: temperature, oxidation, light and UV-radiation.

People using retinoid containing preparations complain of skin irritation. This is the so-called retinoid reaction (often called retinoid dermatitis) and is characterised by redness, dryness and scaling of the skin.

It is known that derivatisation sometimes can eliminate these drawbacks. Vitamin A alcohol (retinol) has been successfully derivatised into e.g. retinyl-acetate and retinyl-palmitate, both of which have improved properties as compared to the alcohol in that they have a reduced instability and irritation-potential. For example, it is known that the vitamin A alcohol is much less stable against heat and light than both ester-derivatives [Kretz, A., SÖFW (1993), 119, pp 21–24]. Therefore, these derivatives are preferably used in cosmetic and pharmaceutical preparations.

However, acetate and palmitate which are used for the derivatisation have no additional skin-advantageous properties. In addition, the in situ formation of active retinoic acid from acetate or palmitate derivatives takes two (enzymatic) conversions, i.e. hydrolysis of the ester bond and oxidation of the free retinol into retinoic acid.

SUMMARY OF THE INVENTION

The present invention relates to new compounds namely active derivatives of sphingoid bases. Specifically, the invention relates to retinoylamide based derivatives of sphingoid bases.

The derivatives consist of a sphingoid base in an amide linkage to retinoic acid or to an analogue of retinoic acid. The sphingoid bases are preferably selected from the group comprising sphingosines, phytosphingosines and sphinganines.

The invention further provides a method for preparing these compounds, wherein the retinoic acid or analogue is chemically coupled either as such or as an activated acid to the sphingoid base.

The compounds of the present invention are used in therapy and/or in cosmetics.

Specifically, the compounds are used in the preparation of compositions for topical application.

DETAILED DESCRIPTION OF THE INVENTION

The present invention relates to new compounds namely active derivatives of sphingoid bases. Specifically, the present invention discloses retinoylamide based derivatives of sphingoid bases.

Sphingoid bases are an important constituent of ceramides. Ceramides form the largest polar lipid class of the epidermal lipids (20–40%) and are a structurally heterogenous group of sphingolipids containing the sphingoid bases sphingosine or phytosphingosine in amide linkage with fatty acids (both hydroxy- and non-hydroxy-fatty acids). Ceramides are supposed to have an essential role in structuring and maintaining the water impermeability barrier of the skin. The structure and flexibilty of the skin can be maintained and/or improved by applying ceramides from outside.

The sphingoid bases to which retinoic acid is coupled include sphingoid bases selected from the group comprising sphingosines, phytosphingosines and sphinganines.

In the present invention, the coupling between retinoid and a sphingoid base is realised through the carboxyl-group of retinoic acid and the free amino-group of the sphingoid base, rendering an amide- rather than an ester-linkage, the latter occurring with the retinol derivatives retinyl-acetate and -palmitate.

The derivatives of the present invention consist of a sphingoid base in an amide linkage to retinoic acid (all-trans retinoic acid) or analogues of retinoic acid, e.g. isotretinoin (13-cis-retinoic acid). The present invention also envisages derivatives which comprise retinol, i.e. retinol which is esterified to one carboxyl group of a dicarboxylic acid whereby the other carboxyl group is involved in the amide linkage with a sphingoid base. The dicarboxylic acids preferably have a chain length of 3–20 carbon atoms.

By coupling retinoic acid to a sphingoid base, ceramide-analogues are formed, in which the acyl group of the ceramide is substituted for a retinoid.

Surprisingly, coupling-products of retinoic acid or analogues with sphingoid bases display similar properties with respect to stability and lack of irritation as the retinol derivatives retinyl-acetate and -palmitate.

Additionally, the compounds of the invention have some advantageous properties related to the properties of ceramides. As a consequence of the more lipophilic character of a retinoyl-sphingoid base, this compound will penetrate deeper into the skin than an unmodified retinoid. Moreover, the penetration into the inner layers of the stratum corneum will occur much faster and more efficiently than with retinoic acid alone.

When the compounds of the invention enter the stratum corneum, retinoic acid is liberated in one hydrolytic step, as a result of in situ enzymatic hydrolysis by an esterase, e.g. lipase, or an amidase, e.g. ceramidase or protease, all of which are present in the mammalian epidermis [see Wertz, P. H. and Downing, D. T., FEBS (1990), 268(1), pp 110–112; Hassler, D. F. and Bell, R. M. in "Ceramidases: Enzymology and metabolic roles", (1993) Adv. Lip. Research 26, pp.49–59 Academic Press, San Diego]. Thus, the derivatives of the invention will target the retinoic acid to sites localised deeper within the skin and allow it to be physiologically active at the proper place, i.e. the mitotically active epidermal cells in the stratum germinativum and/or stratum spinosum.

The present invention provides the additional advantage that, as a result of its incorporation into a sphingoid base, much lower concentrations of retinoic acid are needed to reach the desired effect. Consequently, the compounds of the present invention will cause much less of the side effects attributed to free retinoic acid, such as redness (erythema), dryness and scaling, i.e. less irritation and inflammation of the skin.

The enzymatic hydrolysis of the compounds of the present invention which occurs in the skin will release the retinoic acid as well as the sphingoid base, ie. phytosphingosine, sphingosine or sphinganine. Sphingoid bases are also known for their biological activity. For instance, sphingoid bases can be beneficial to the skin by (a) serving as a building block for new ceramides, (b) inducing de novo biosynthesis of ceramides and (c) acting as an important physiological regulator of growth and differentiation of epidermal cells (Hannun, Y. A. and Bell, R. M., Science 1989, 243, pp. 500–507).

The present invention further provides a method for preparing retinoic acid derivatives of sphingoid bases. The retinoylamide derivatives of sphingoid bases of the present invention can be prepared by various synthesis methods known to the skilled person. The retinoic acid can be coupled to a sphingoid base either enzymatically or chemically. chemically, the acid can be coupled either as such using coupling reagents, e.g. EEDQ (N-ethoxycarbonyl-2-ethoxy-1,2-dihydroquinoline), HOBT (hydroxybenzotriazole) or a carbodiimide, or as an activated acid e.g. a mixed anhydride or acid halogenide.

Preferably, the compounds of the present invention are prepared by the following reaction steps:

- retinoic acid is reacted with an alkyl sulfonyl chloride or an alkyl phenyl sulfonyl chloride, in an organic solvent and in the presence of an organic base to form the corresponding mixed anhydride,
- the mixed anhydride is reacted with a sphingoid base, e.g. phytosphingosine, or a salt thereof to form the corresponding N-acyl sphingoid base,
- the N-acyl sphingoid base is subjected to alkaline hydrolysis to obtain the retinoylamide based derivatives of sphingoid bases.

Phytosphingosine is obtainable efficiently by deacetylation of tetra-acetylphytosphingosine (TAPS), which on its turn can be obtained in large amounts by microbial fermentation, especially by fermentation of *Pichia ciferri*.

Another aspect of the invention relates to the use of these compounds in the preparation of cosmetic and/or pharmaceutical compositions.

Specific cosmetic preparations include the usual components.

The composition comprises a vehicle to enable the active ingredient to be conveyed to the skin. Vehicles include water, solids and liquids. These are classified as emollients, emulsifiers, surfactants, solubilizers, propellants, solvents, humectants, thickeners and powders.

Emollients include alkyl higher fatty acids, natural oils, higher fatty alcohols, glyceryl and isopropyl esters, mineral oils, silicones, fatty alcohol esters.

Emulsifiers comprise compounds having a HLB (hydrophilic/lipophilic balance) value which is in the lower as well as in the higher ranges, i.e. compounds which are able to form a water-in-oil as well as compounds which are able to form an oil-in-water emulsion, respectively. Typically, if a water-in-oil emulsion is required, the HLB value of the emulsifier or mixture of emulsifiers varies between about 1 and 7. For an oil-in-water emulsion, said HLB value is higher than about 7.

Propellants include propane, butane, isobutane, dimethyl ether, chlorofluoroalkanes, carbon dioxide, nitrous oxide.

Solvents include ethyl alcohol, methylene chloride, isopropanol, ethyl ethers, DMSO, propylene glycol, butylene glycol.

Humectants include proteins and protein hydrolysates, amino acids, sorbitol, glycerin, other polyols.

Thickeners include polysaccharides, gums and carboxylic group-containing polymers Powders including chalk, talc, starch.

The combination of the said components can account for 5 to 99% of the composition.

The compositions containing the compounds of the invention are suitable for topical use. The amount of active ingredient or mixture thereof suitable for topical application ranges from 0.0001% to 25%, preferably from 0.005% to 5%, most preferably from 0.01 to 2% by weight of the composition.

The compositions containing the compounds of the invention are advantageously used in those fields where application of retinoids is desired, e.g. for the treatment of acne, psoriasis and UV-damaged skin.

5

The present invention is exemplified by the following not restrictive examples.

EXAMPLE 1

Synthesis of N-(retinoyl)-phytosphingosine

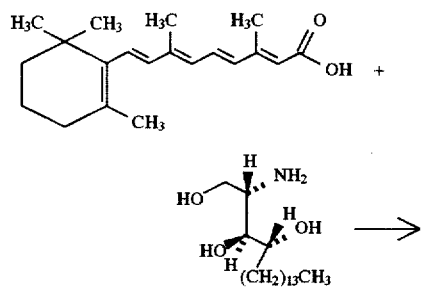

A mixture of retinoic acid (98%, Janssen Pharmaceuticals; 5.0 g; 16.3 mmoles), triethyl amine (17 ml) and chloroform (260 ml) was stirred at 40 °C. under nitrogen until a clear solution was obtained. After adding tosyl chloride (3.0 g; 15.5 mmoles) stirring was continued at 40° C. for 1 hour. Then phytosphingosine (4.0 g; purity 94%; 11.8 mmoles) was added and, after stirring the reaction mixture under nitrogen for one hour at 40° C., water (25 ml) was added. The layers were separated and 25 ml of water was added to the organic layer. After adjusting the pH at 2.5 with HCl (36%) the organic layer was separated, washed with a sodium chloride solution (10 ml; 20%-solution) and evaporated to dryness in vacuo at a rotavapor.

Then 10 ml of methanol was added and the methanol was evaporated again. After dissolving the residue in 20 ml of warm methanol the solution was cooled down to 1° C. and filtrated with an isolated filter in order to keep the temperature low. After washing with 5 ml of cold methanol and drying in vacuo the N-(retinoyl)-phytosphingosine was obtained.

EXAMPLE 2

Preparation of oil-in-water and water-in-oil emulsions containing retinoyl-phytosphingosine Preparation procedure water-in-oil emulsion The oil soluble components pos. 1–8 (see Table 1) are melted at approx. 80° C. A slightly turbid solution results, which has no crystals in it. The clear water phase (pos. 9–12) is also heated up to 80° C. and is added slowly under vigorous stirring to the oil phase. This hot emulsion is passed through a rotorstator homogenizer (Type Homozenta, Pelui AG, smallest gap width) and then cooled down to room temperature with a normal laboratory stirrer.

TABLE 1

Composiiton of W/O-emulsion

| Pos. | Raw material | % | Chemical description |
|---|---|---|---|
| 1 | Cetiol LC | 10,00 | Coco Caprylate/Caprate, oil |
| 2 | Paraffin oil perliquidum | 10,00 | Mineral Oil, oil |
| 3 | Arlacel 481 | 9,00 | Glyceryl Sorbitan Oleostearate, emulsifier |
| 4 | Cetiol V | 8,00 | Decyl Oleate, oil |
| 5 | Elfacos C 26 | 5,00 | Hydroxyoctacosanyl Hydroxystearate, consistency regulating factor |
| 6 | Vaseline | 2,00 | Petrolatum, oil |
| 7 | Phenonip | 0,60 | Mixture of Parabenes, preservative |
| 8 | Retinoyl-PS | 0,05–0,5 | Retinoyl-phytosphingosine |
| 9 | Karion F fluid | 5,00 | Sorbitol, Humidity Factor |
| 10 | Glycerin 86–88% | 3,00 | Glycerin, Humidity Factor |
| 11 | Trilon B fest | 0,10 | EDTA, Sequestering Agent |
| 12 | Demineralized water | ad 100,00 | Water |

-continued

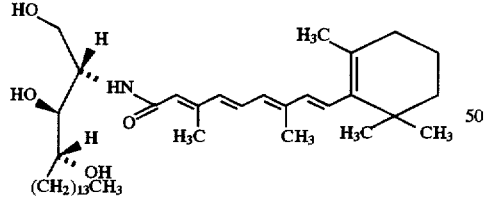

Preparation procedure oil-in-water emulsion

The oil-soluble components pos. 1–12 (see Table 2) are melted at approx. 80° C. A slightly turbid solution results, which has no crystals. Pos. 18 is added slowly to pos. 19 (Ultra Turrex) and is treated in that way for 15–30 minutes. The solution of Pos. 13–17 are added to this carbopol-dispersion, which becomes a gel thereby, heated to 80° C. and then added slowly under vigorous stirring to the oil phase. The emulsion is cooled down to room temperature with a normal laboratory stirrer without further homogenization.

TABLE 2

Composition of O/W-emulsion

| Pos. | Raw material | % | Chemical description |
|---|---|---|---|
| 1 | Cetiol S | 8,00 | Dioctylcyclohexane, oil |
| 2 | Cutina GMS | 2,20 | Glyceryl Stearate, consistency factor |
| 3 | Vaseline | 2,00 | Petrolatum, oil |
| 4 | Puroba öl | 2,00 | Jojoba Oil, oil |
| 5 | Arlatone 983 S | 1,50 | POE-fatty acid ester, emulsifier |
| 6 | Brij 76 | 1,50 | POE-10-stearyl alcohol, emulsifier |
| 7 | PCL-Liquid | 1,00 | Cetearyl Octanoate, emollient |
| 8 | Softisan 100 Pastllen | 1,00 | Hydrogenated Coco Glycerides, consistency factor |
| 9 | Arosol | 0,70 | Phenoxyethanol, preservative |
| 10 | Abil 350 | 0,50 | Silicon Oil, oil |
| 11 | Retinoyl-PS | 0,5–1,0 | Retinoyl-phytosphingosine |
| 12 | Propylparaben | 0,05 | Parahydroxybenzoic acid propylester, preservative |
| 13 | Glycerin 86–88% | 2,00 | Glycerin, humidity factor |
| 14 | Propylenglycol | 1,50 | Propylene Glycol, humidity factor |
| 15 | NaOH 50% | 0.76 | Sodium Hydroxide |
| 16 | Methylparaben | 0,10 | Parahydroxybenzoic acid methylester, preservative |
| 17 | Trilon BD | 0,10 | Disodium EDTA, sequestering agent |
| 18 | Carbopol 941 | 0,30 | Carbomer, thickening agent |
| 19 | Demineralized water | ad 100,00 | Water |

We claim:

1. A compound which is a sphingoid base linked through an amide to retinoic acid or a retinoic acid analogue.

2. A compound which is a sphingoid base linked through an amide to a dicarboxylic acid esterified to retinol.

3. A compound according to claim 1, characterized in that the sphingoid base is selected from the group comprising sphingosines, phytosphingosines and sphinganines.

4. A method for preparing a compound according to claim 1 characterized in that the acid is chemically coupled either as such or as an activated acid to the sphingoid base.

5. A cosmetic or pharmaceutical composition comprising a compound according to claim 1.

6. A method of using a compound according to claim 1 comprising administering a therapeutically effective amount of said compound to a subject.

7. A method of using a compound according to claim 1 comprising topically applying said compound, wherein said compound is in a cosmetic formulation.

8. The method according to claim 6 wherein said administration is topical.

* * * * *